United States Patent
Van Dijk et al.

(10) Patent No.: US 8,120,002 B2
(45) Date of Patent: Feb. 21, 2012

(54) MULTI-COLOR BIOSENSOR FOR DETECTING LUMINESCENCE SITES ON A SUBSTRATE HAVING A REFRACTIVE OPTICAL ELEMENT FOR ADJUSTING AND FOCUSING AT LEAST TWO INCIDENT IRRADIATION BEAMS OF DIFFERENT WAVELENGTHS

(75) Inventors: Erik Martinus Hubertus Petrus Van Dijk, Eindhoven (NL); Marinus Iosif Boamfa, Eindhoven (NL); Reinhold Wimberger-Friedl, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 215 days.

(21) Appl. No.: 12/374,006

(22) PCT Filed: Jul. 5, 2007

(86) PCT No.: PCT/IB2007/052634
§ 371 (c)(1),
(2), (4) Date: Jan. 15, 2009

(87) PCT Pub. No.: WO2008/012706
PCT Pub. Date: Jan. 31, 2008

(65) Prior Publication Data
US 2009/0309049 A1   Dec. 17, 2009

(30) Foreign Application Priority Data
Jul. 20, 2006   (EP) .................................... 06117547

(51) Int. Cl.
*G01N 21/86* (2006.01)
(52) U.S. Cl. ..................................... 250/559.4; 250/216
(58) Field of Classification Search ............. 250/559.4, 250/559.41, 559.44, 216, 234, 458.1, 461.2; 356/4.04–4.06, 317–324, 244–246
See application file for complete search history.

(56) References Cited

U.S. PATENT DOCUMENTS

| | | | |
|---|---|---|---|
| 4,980,549 A | 12/1990 | Baldwin | |
| 5,296,700 A * | 3/1994 | Kumagai | 250/216 |
| 5,790,242 A * | 8/1998 | Stern et al. | 356/4.04 |
| 6,185,030 B1 | 2/2001 | Overbeck | |

(Continued)

FOREIGN PATENT DOCUMENTS
DE   19733193 A1   2/1999
(Continued)

OTHER PUBLICATIONS

Hendriks B H W et al: "Application of nonperiodic phase structures in optical systems" Applied Optics, OSA, Optical Society of America, Washington, DC, US, vol. 40, No. 35, Dec. 10, 2001, pp. 6548-6560, XP002264634 ISSN: 0003-6935.
Hendriks B H W et al: "High-NA achromatic objective lens" Optical Memory and Optical Data Storage Topical Meeting, 2002. International Symposium on Jul. 7-11, 2002, Piscataway, NJ, USA IEEE, Jul. 7, 2002, pp. 395-397, XP010600236 ISBN: 0-7803-7379-0.

(Continued)

*Primary Examiner* — Que T Le

(57) ABSTRACT

A detection system for detecting luminescence sites on a substrate and including an irradiation unit for generating at least one excitation irradiation beam for exciting luminescence sites on the substrate; a first optical element, e.g. refractive element adapted for receiving at least two irradiation beams of different wavelengths or wavelength ranges, the at least two irradiation beams being excitation irradiation beam(s) to be focused on a substrate and/or luminescence irradiation beam(s) to be collected from the excited luminescence sites on the substrate; and an optical compensator for adjusting at least one of the at least two irradiation beams of different wavelengths or wavelength ranges so as to reduce or compensate for optical aberrations.

17 Claims, 7 Drawing Sheets

U.S. PATENT DOCUMENTS

| | | |
|---|---|---|
| 6,355,934 B1 | 3/2002 | Osgood et al. |
| 6,617,590 B2 | 9/2003 | Nishioka et al. |
| 2004/0042007 A1 | 3/2004 | Osipchuk et al. |

FOREIGN PATENT DOCUMENTS

| | | |
|---|---|---|
| DE | 10063276 A1 | 7/2002 |
| EP | 1349201 A1 | 10/2003 |
| WO | 9728439 A1 | 8/1997 |
| WO | 2004077122 A1 | 9/2004 |
| WO | 2005010590 A1 | 2/2005 |

OTHER PUBLICATIONS

Knittel J et al: "Liquid crystal lens for spherical aberration compensation in a blu-ray disc system" IEE Proceedings: Science, Measurement and Technology, IEE, Stevenage, Herts, GB, vol. 152, No. 1, Jan. 3, 2005, pp. 15-18, XP006023334 ISSN: 1350-2344.

Shi Yan et al: "Design of scanning objective lens for dual-laser biochip analyzer" Journal of Zhejiang University Zhejiang Univ China, vol. 39, No. 7, Jul. 2005, pp. 1056-1059, XP002467080 ISSN: 1008-973X.

* cited by examiner

MULTI-COLOR BIOSENSOR FOR DETECTING LUMINESCENCE SITES ON A SUBSTRATE HAVING A REFRACTIVE OPTICAL ELEMENT FOR ADJUSTING AND FOCUSING AT LEAST TWO INCIDENT IRRADIATION BEAMS OF DIFFERENT WAVELENGTHS

FIELD OF THE INVENTION

The present invention relates to the field of optical detection. More particularly, the present invention relates to methods and systems for optical detection such as detection of luminescent signals, e.g. as used in qualitative or quantitative detection of biological, chemical or bio-chemical analysis, e.g. using particles or fluorophores, and to means for improving such detection methods and systems.

BACKGROUND OF THE INVENTION

An image reading apparatus is described (U.S. Pat. No. 6,617,590) which includes three laser sources, a scanning mechanism for scanning a surface with a laser beam emitted from the laser sources, a light detector and a confocal optical system for leading light emitted from the image carrier to the light detector. The apparatus makes provision for a number of relevant detection techniques such as microarray imaging, autoradiographic imaging, chemiluminescent imaging and more. It includes a confocal switching member having pinholes of different diameters and disposed between the confocal optical system and the light detector. A drawback of the above described apparatus is that chromatic aberrations of the confocal lens are neglected thereby limiting simultaneous multi-color detection.

Fluorescence is a phenomenon that is used routinely in life science research. Fluorescent probes and conjugations are used extensively to trace the whereabouts of cellular components and protein localization, and to detect particular components e.g. biomolecules in complex biomolecular assemblies, including live cells, with exquisite sensitivity and selectivity.

A fluorescent probe is a fluorophore designed to localize within a specific region of a biological specimen or to respond to a specific stimulus. Multicolor labeling experiments entail the deliberate introduction of two or more probes to monitor different biochemical functions simultaneously. This technique has major applications in analytic techniques such as flow cytometry, DNA sequencing, fluorescence in situ hybridization (FISH), fluorescence microscopy, fluorescence spectroscopy, fluorescence resonance energy transfer (FRET), fluorescence recovery after photobleaching (FRAP), etc.

SUMMARY OF THE INVENTION

At present, simultaneous multi-color detection is severely restricted by the limitations of current optical detection devices, or by the costs involved.

Signal isolation and data analysis are facilitated by maximizing the spectral separation of the multiple emissions. Consequently, fluorophores with narrow spectral bandwidths are particularly useful in multicolor applications. An ideal combination of dyes for multicolor labeling would exhibit strong absorption at a coincident excitation wavelength and well-separated emission spectra. There is a need for single dyes with the requisite combination of a large extinction coefficient for absorption and a large wavelength (Stokes) shift. These are difficult to find. Moreover, multiple wavelengths focusing often implies expensive and complicated optical systems such as imaging lens assemblies, movable parts to bring the sample in focus such as in microscopes, or tilting parts.

An object of the present invention is to obtain good methods and systems for optical detection such as detection of luminescent signals, e.g. detecting emissions from biological, chemical or bio-chemical particles. It is an advantage of embodiments of the present invention that efficient and high quality detection can be obtained. It is also an advantage of embodiments of the present invention that high quality detection can be obtained in a system using only a single optical element, e.g. refractive element, for focusing different irradiation beams of different wavelengths or wavelength ranges on the substrate.

It is an advantage of particular embodiments of the present invention that spherical and chromatic aberration caused by the inability of a refractive element to bring multiple wavelengths of light to focus at a single point is reduced.

It is an advantage of particular embodiments of the present invention that sharper focus can be obtained without the need to adjust all of the optical elements or only minimal adjustment, i.e. without correction lenses or complex lens assemblies.

Advantages of particular embodiments of the present invention also include the use of fixed elements (no movable parts) which makes the device more robust and less susceptible to wear, as well as the provision of a single optical element, e.g. refractive element for both focusing and collecting light.

It is also an advantage of particular embodiments of the present invention that a broad range of applications can be run on the system and that a broad range of labels can be used thanks to multiple wavelength excitation and collection in an aberration-low or aberration-free operation.

The above objective is accomplished by methods and devices according to the present invention.

The present invention relates to a detection system for detecting luminescence sites on a substrate, the detection system comprising an irradiation unit for generating at least one excitation irradiation beam for exciting luminescence sites on the substrate, a first optical element, e.g. first refractive element, adapted for receiving at least two irradiation beams of different wavelengths or wavelength range, the at least two irradiation beams being excitation irradiation beam(s) to be focused on a substrate and/or luminescence irradiation beam(s) to be collected from the excited luminescence sites on the substrate, and an optical compensator for adjusting at least one of the at least two irradiation beams of different wavelengths or wavelength range so as to at least partly compensate for optical aberrations. The adjusting may be selectively adjusting. The optical aberrations may be aberrations induced by the first optical element, e.g. the first refractive element. It may be chromatic aberrations in any or both of the excitation and/or luminescence irradiation beam, each having irradiation at a characteristic, different wavelength or in a characteristic different wavelength range. The two irradiation beams may be a single excitation irradiation beam and the luminescence irradiation beam to be collected. It is an advantage of particular embodiments according to the present invention that a system whereby irradiation beams of different wavelengths or wavelength range are refracted by the same optical element, e.g. the same refractive element, are obtained, wherein aberrations are reduced or even avoided. The latter allows that systems may be provided making use of a standard and/or cheap optical element, e.g. refractive element, for focusing the at least one excitation radiation beam on the substrate. The detection system furthermore may comprise a detection unit having at least a second optical element, e.g. second refractive element, for focusing the luminescence irradiation beam onto at least one detector element. The detection unit may comprise a pixelated detector. It is an advantage of particular embodiments according to the present invention that aberration for irradiation beams can be reduced, while making use of a standard and/or cheap optical element, e.g. refractive element. The first optical element, e.g. first refractive element, may be the objective lens of the system.

The irradiation unit may be adapted for generating at least two excitation irradiation beams of different wavelength or wavelength range and the first optical element, e.g. first refractive element, may be adapted for receiving the at least two excitation irradiation beams. It is an advantage of particular embodiments according to the present invention that multiple excitation with different irradiation wavelengths can be used in a detection system and method whereby the amount of aberration occurring for the different irradiation at different wavelengths or wavelength ranges is reduced. This can enable multiplexing i.e. operating with multiple labels, resulting in a temporal and economical reduction of cost. It also can enable multi-color excitation, aberration-free or aberration-poor, detection with high sensitivity. It is an advantage of embodiments according to the present invention that methods and systems suitable for a wide variety of labels are obtained, as e.g. labels with smaller Stokes shifts can successfully be detected. The first optical element, e.g. refractive element, may be adapted for receiving the at least two excitation irradiation beams by its position.

The optical compensator may introduce at least a phase shift in one of the irradiation beams. The optical compensator may be a phase plate.

The optical compensator may introduce at least a phase shift in one of the excitation irradiation beams for focusing the excitation irradiation beam(s) at the same focus on the substrate. It is an advantage of particular embodiments of the present invention that an appropriate light path is generated for at least two irradiation beams of different wavelengths or wavelength ranges using only a single optical element.

The optical compensator and the first optical element, e.g. refractive element, may be separate elements. This enables cost-effective production of the detection system as a maximum of existing part can be integrated from existing mass-produced, low-cost optical pick-up units, and a commercially available lens can be used. The optical compensator may be incorporated into the first optical element, e.g. first refractive element. It is an advantage of particular embodiments of the present invention that the detection system may be robust. The detection system may be adapted for selecting one of the at least two irradiation beam to be used at a time. It is an advantage of particular embodiments of the present invention that the most appropriate excitation wavelength can be selected for detecting luminescence sites on the substrate.

The irradiation unit may be adapted for generating at least two of the at least two excitation irradiation beams simultaneously. It is an advantage of particular embodiments of the present invention that simultaneous excitation and detection reduces the overall analysis time or allows to increase the sensitivity within a fixed time span. The irradiation beams may be received in different distinct periods.

The detection system furthermore may comprise a detection unit having at least a detector element and optical elements for focusing the at least two luminescence irradiation beams as parallel luminescence irradiation fields on the detector element. It is an advantage of particular embodiments of the present invention that each irradiation beam may pass a second optical element, e.g. second refractive element, close to the optical axis of the second optical element, e.g. second refractive element, i.e. that the average distance of each of the irradiation beams to the optical axis of the second optical element, e.g. second refractive element, is small.

The detection system furthermore may comprise a detection unit having at least a detector element and optical elements for focusing the at least two luminescence irradiation beams as neighboring luminescence irradiation fields lying in line on the substrate. It is an advantage of particular embodiments of the present invention that simultaneously distinct luminescence information may be obtained from the different luminescence irradiation fields.

The detection system may comprise a detection unit adapted for simultaneously detecting different luminescence irradiation beams from the luminescence sites, the different luminescence irradiation beams each having a substantially different wavelength. It is an advantage of particular embodiments of the present invention that multiplexing can be enabled, i.e. that multiple labels can be used simultaneously, thereby reducing the economical and temporal cost for detection.

The at least two excitation irradiation beams being a first, a second and a third irradiation beam may have an average wavelength in a wavelength ranges of 760 nm to 800 nm, 640 nm to 680 nm, and 380 nm to 420 nm, respectively.

It is an advantage of particular embodiments of the present invention that parts of the biosensor can be obtained from existing mass-produced, low-cost optical pick-up units allowing to obtain detection systems in a cost effective manner.

The present invention also relates to an optical compensator for adjusting at least one of at least two incident irradiation beams of different wavelength or wavelength range, the optical compensator being adapted for focusing the at least two incident irradiation beams at a same focus on a substrate using a same optical element, e.g. refractive element.

The adjusting may be selectively adjusting.

The optical compensator may be adapted by non-periodic phase structures. It is an advantage of particular embodiments of the present invention that for the manufacturing of the optical compensator, after designing the optical compensator, well known techniques can be used.

The optical compensator may be a phase wheel having different non-periodic phase structures through which the at least two irradiation beams are arranged to pass.

The present invention also relates to a method for detecting radiation sites on a substrate, the method comprising generating at least one excitation irradiation beam for exciting luminescence sites on the substrate, guiding, e.g. refracting, at least two irradiation beams of different wavelength or wavelength range, the at least two irradiation beams being excitation irradiation beam(s) to be focused on the substrate and/or luminescence irradiation beam(s) to be collected from the excited luminescence sites on the substrate, and adjusting one of the at least two irradiation beams of different wavelengths or wavelength ranges so as to at least partly compensate for optical aberrations.

Generating at least one excitation irradiation beam may comprise generating at least two excitation irradiation beams, guiding, e.g. refracting, at least two irradiation beams may comprise focusing at least two excitation irradiation beams on the substrate, and adjusting one of the at least two irradiation beams may comprise adjusting at least one of the at least two excitation irradiation beams to create a common focus on the substrate.

The present invention also relates to a computer-based method for designing an optical compensator, the method comprising obtaining information about the wavelength or average wavelength of each of at least two irradiation beams of different wavelength or wavelength range, obtaining information about the position and optical characteristics of an optical element, e.g. refractive element, used for focusing the at least two irradiation beams, and determining optimal feature parameters of an optical compensator such that optical aberrations are reduced for the at least two irradiation beams taking into account that a same focus is to be obtained for the at least two irradiation beams focused by the single optical element, e.g. single refractive element.

The present invention furthermore relates to a computer program product for executing the computer based method for designing an optical compensator comprising obtaining information about the wavelength or average wavelength of each of at least two irradiation beams of different wavelength or wavelength range, obtaining information about the position and optical characteristics of an optical element, e.g. refractive element, used for focusing the at least two irradiation beams, and determining optimal feature parameters of an optical compensator such that optical aberrations are reduced for the at least two irradiation beams taking into account that a same focus is to be obtained for the at least two irradiation beams focused by the single optical element, e.g. single refractive element.

The present invention also relates to a machine readable data storage device storing the computer program product as described above and/or to transmission of such a computer program product over a local or wide area telecommunications network.

This and other objects and advantages of the invention are provided by one or more of the embodiments described below.

Particular and preferred aspects of the invention are set out in the accompanying independent and dependent claims. Features from the dependent claims may be combined with features of the independent claims and with features of other dependent claims as appropriate and not merely as explicitly set out in the claims. The teachings of the present invention permit the design of improved methods and apparatus for multiple wavelength focusing in a biosensor.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

SHORT DESCRIPTION OF THE FIGURES

Figure 1:
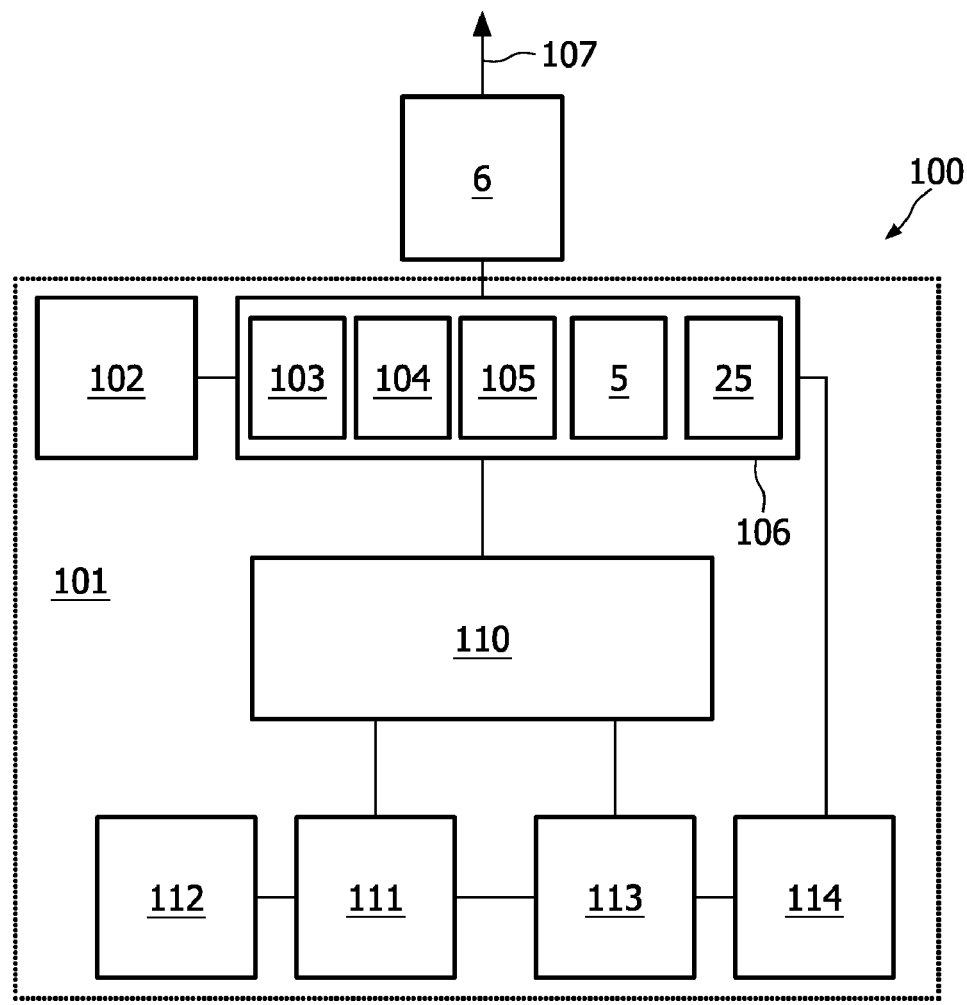
FIG. 1 is a schematic illustration of a detection system according to an embodiment of a first aspect of the present invention.

In the different figures, the same reference signs refer to the same or analogous elements.

DETAILED DESCRIPTION OF EMBODIMENTS

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art. With the term "irradiation" and "luminescence" typically UV, visible or infrared irradiation may be meant although the invention is not limited thereto and other types of electromagnetic irradiation also could be used. The wavelength of the irradiation beam referred to may be the average wavelength of the irradiation beam or the wavelength at which the maximum emission is obtained. The term "substrate", as used herein, describes the field on which the irradiation beam(s) have to be focused and from where luminescence irradiation beam(s) is (are) collected. Luminescence sites of which detection is envisaged according to the present invention are distinct sites or spots on a substrate that emit at least one luminescence beam having at least one luminescence beam wavelength or at least one central luminescence beam wavelength. Any luminescent signal such as reflection, scattering, fluorescence, chemiluminescence, electroluminescence, bioluminescence, or other luminescence is envisaged. Luminescence sites are also provided by structural features of a surface that scatter or reflect light. Luminescence sites may relate to occupied sites on a substrate, e.g. occupied by luminescent labeled target particles. Molecules that emit light or change their light output, e.g. extinguish or at least partly extinguish or change the color of the emitted light when close to or bound to an analyte molecule will be described as "optically variable molecules". Luminescence emanating from a substrate includes light that is transmitted away from and/or through the substrate, or is created by elements placed on the substrate, for example, fluorescent labels that create fluorescent light, e.g. within a microarray after excitation with an appropriate wavelength of light, or is created by structural features of the surface of the substrate such as light-scattering gratings. The substrate may be any suitable substrate, e.g. a glass slide, a microarray, a silicon chip, a membrane e.g. a nylon membrane, a filter e.g. a nylon filter, a microfluidic device, a roughened metal substrate, a gel e.g. an agarose gel containing stained DNA or proteins, or any other device having a suitable surface for providing luminescence sites. The term "sample", as used herein, relates to a composition comprising analyte(s) of interest. The term "analyte", as used herein, refers to a substance to be detected by the methods of the present invention. The analyte may be an inherent luminescence provider or may be labeled to emanate luminescence. The term "label", as used herein, refers to a molecule or material capable of generating a detectable signal. The labels may be attached directly to the analyte or through a linker moiety, e.g. a labeled probe. These probes, intended to either specifically bind to the analyte, are obtained by linking a compound capable of specifically binding to the analyte or corresponding to at least (a specific) part of the analyte, to a label. The nature of the analyte-specific probe will be determined by the nature of the analyte to be detected. Most commonly, the probe is developed based on a specific interaction with the analyte such as, but not limited to antigen-antibody binding, complementary nucleotide sequences, carbohydrate-lectin binding, complementary peptide sequence binding, ligand-receptor binding, coenzyme-enzyme binding, enzyme inhibitor-enzyme binding, etc.

According to a first aspect, the present invention provides a detection system for detecting luminescence sites from a substrate. Such a detection system may be for example a detection system for detecting chemical, biological or biochemical analytes, e.g. in the form of particles but the invention not being limited thereto. Such a detection system typically comprises an irradiation unit for generating at least one excitation irradiation beam for irradiating a substrate. Such an at least one excitation irradiation beam typically may result in excitation of the luminescence sites at the substrate, thus resulting in at least one luminescence irradiation emission. The detection system typically may comprise a first optical element, e.g. first refractive element, adapted for receiving at least two irradiation beams of different wavelengths, whereby the at least two irradiation beams are excitation irradiation beams generated by the irradiation unit. These beams are to be focused using the first optical element, e.g. first refractive element on the substrate and/or the luminescence irradiation beams from the excited luminescence sites on the substrate are to be collected by the first optical element, e.g. first refractive element. According to the first aspect, the detection system therefore also comprises an optical compensator for adjusting at least one of the at least two irradiation beams, in order to reduce or at least partly compensate for optical aberrations induced by the single optical element, e.g. single refractive element. Such optical aberrations typically may be induced by the use of a single, first optical element, e.g. refractive element, for guiding, e.g. refracting irradiation beams having a different wavelength, such as e.g. different excitation irradiation beams, an excitation irradiation beam and a luminescence irradiation beam or different luminescence irradiation beams. A schematic overview of a detection system 100 comprising essential and optional components is shown by way of illustration in FIG. 1. The detection system 100 is suitable for detecting light emission sites on a sample 6. As shown in FIG. 1, the detection system 100 comprises an irradiation unit 102, an optical element 25, e.g. refractive element 25 adapted for receiving at least two irradiation beams of different wavelength and an optical compensator for reducing or correcting optical aberrations introduced in the irradiation beams by the optical element 25, e.g. refractive element 25. The above components and additional or optional components of the exemplary detection system as shown in FIG. 1 will be further described in more detail below.

As set out above, the detection system 100 typically comprises an irradiation unit 102 comprising at least one irradiation source. The at least one irradiation source may be any irradiation source suitable for use in a detection system, such as e.g. a light source. The at least one irradiation beam has an at least one predetermined wavelength $\lambda$. The at least one irradiation source may be an illumination array comprising radiation sources, such as lasers, emitting excitation irradiation beams having radiation at wavelengths $\lambda_1, \lambda_2, \lambda_3, \ldots, \lambda_n$, or emitting radiation in predetermine wavelength ranges, for irradiating the substrate. The irradiation source also may comprise a white light source which may be filtered to several irradiation beams having radiation at a specific wavelength or in a specific wavelength range. The irradiation source also may comprise one or more monochromatic or quasi monochromatic optical sources such as lasers or discharge lamps or light emitting diodes. The light source may comprise argon lasers, diode lasers, helium lasers, dye lasers, titanium sapphire lasers, Nd:YAG lasers or others. The irradiation unit may for example comprise a tuneable irradiation source, such as e.g. a tuneable semiconductor laser, for sequentially supplying at least one irradiation beam, or at least one semiconductor laser for simultaneously or consecutively supplying at least one radiation beam. The at least one irradiation source thus may be a plurality of irradiation sources e.g. two or three irradiation sources. The latter typically allows multiplexing. The at least one irradiation source is adapted for emitting radiation, e.g. light, at a predetermined wavelength or a predetermined wavelength range, suitable for exciting or irradiating luminescence sites, e.g. luminescence sites like fluorescence sites. Such sites may comprise for example optically variable particles, present in the sample. For example, in the case where the generated radiation is fluorescence radiation, the optical wavelength of the excitation radiation typically may be e.g. in the range from 200 nm to 2000 nm, or e.g. in the range from 400 nm to 1100 nm, the invention not being limited thereto. In a preferred embodiment, the irradiation unit 102 may be adapted for scanning a substrate to be studied with the at least one irradiation beam generated. The excitation field of the at least one irradiation beam may be a single spot, an elongated spot or a row of partly overlapping spots. Using an at least piecewise elongated spot allows for exciting different areas of the substrate, which if detected distinctively, results in simultaneous detection of occupation of different binding sites. The latter therefore may result in efficient methods for detection.

The detection system 100 furthermore comprises a first optical element 25, e.g. first refractive element 25, that is positioned such that it receives at least two irradiation beams having a different wavelength. Such irradiation beams may be excitation irradiation beams generated by the irradiation unit 102, luminescence irradiation beams collected from luminescence sites on the substrate, excited by the excitation irradiation beams, or a combination of one or more excitation irradiation beams and one or more luminescence irradiation beams. Such a first optical element 25 may be a refractive element 25 such as e.g. a conventional or standard refractive element, such as e.g. an objective lens as used in an optical storage device. The first optical element 25, e.g. first refractive element 25, typically may be the objective lens in the detection system used for focusing the excitation irradiation beam(s) on the substrate. The optical element however also may be a parabolic mirror, as well as a number of other dioptric, catoptic, and catadioptric imaging means, including a prism, adapted for receiving at least two irradiation beams of different wavelength. As described above, the first optical element 25, e.g. the first refractive element 25, alternatively or in addition thereto may be used both for focusing the excitation irradiation on the substrate and for collecting the luminescence irradiation, if present, from the substrate. Typically such a detection system 100, or more particularly the optical element 25, e.g. first refractive element 25, used in common for different irradiation beams, is optimized for one particular wavelength. Using the same first optical element 25, e.g. first refractive element 25 for irradiation beams having multiple wavelengths causes optical aberrations, e.g. chromatic aberrations, as an optical element, e.g. refractive element, typically is adapted for a first predetermined wavelength, leading to aberrations if irradiation beams having other predetermined wavelengths pass through the optical element, e.g. refractive element 25.

The detection system also comprises an optical compensator 5 for reducing or at least partly compensating for optical aberrations induced by using a single optical element, e.g. single refractive element, for different irradiation beams having different wavelengths, positioned such that the irradiation beams having different wavelengths and passing through the single optical element, e.g. single refractive element, also encounter the optical compensator on their optical path. In general, the optical compensator typically introduces differences in optical path distance (OPD) for the different irradiation beams in order to correct for the optical aberrations induced by the optical element, e.g. refractive element used for different irradiation beams having different wavelength. Furthermore, correction for optical aberrations induced by other optical elements also may be corrected. The introduction of differences in optical path distance may be e.g. performed by introducing phase shifts. Such phase shifts may be such that for one of the irradiation beams the phase shift, modulo $2\pi$, may be substantially zero, or it may be different from substantially zero for all irradiation beams envisaged. The optical compensator at least partly may compensate, it is it may reduce, the average optical aberrations caused by multiple irradiation beams of different wavelengths. If several excitation irradiation beams of different wavelength are used with a single optical element, e.g. single refractive element, the reduction or compensation may be such that the different excitation irradiation beams can be focused to the same focus on the substrate. In other words, the optical compensator may reduce or at least partly compensate for optical aberrations thus bringing different wavelengths into a common focus. It is an advantage of embodiments of the present invention that the optical compensator can be used in conjunction with optical elements from optical pick-up units for running a number of relevant bioassays in a cost effective manner. The optical compensator may be any suitable optical compensator 5 allowing to at least partly correct for such optical aberrations, such as e.g. a phase plate. The optical compensator 5 may for example be a diffractive element that diffracts the irradiation beams such that the irradiation beam with the shortest wavelength undergoes an introduced phase change (modulo $2\pi$) that is substantially 0, while at least one of the other irradiation beams is diffracted according to a first order diffraction. Another example of an optical compensator may e.g. be a diffractive element having a stepped profile which approximates a blazed diffraction grating, whereby a zero$^{th}$ diffraction order is selected for an irradiation beam with shortest wavelength and a first order and/or higher order diffraction is selected for at least one of the other irradiation beams. The optical compensator 5 for example also may be an optical element comprising non-periodic phase structures (NPSs) for reducing or at least partly compensating a wavefront aberration of at least one of the irradiation beams, whereby the phase structure comprises birefringent material and has a non-periodic stepped profile. Typically birefringent materials are used in combination with different polarization states of light used. Another example of an optical compensator 5 is based on non-periodic phase structures (NPSs) providing basic radial zone profiles introducing a constant phase across their width superimposed with an additional radial surface profile wherein the non-periodic phase structures introduce a variable phase. In this exemplary optical compensator, the phase changes introduced by the optical compensator may be different from zero for all the irradiation beams, thereby possibly even introducing small aberrations for one irradiation beams, but improving the average amount of aberrations when the optical aberrations for all irradiation beams are taken into account. It is to be noticed that the above examples of optical compensators are only provided by way of illustration, the present invention not being limited thereto. Another example of an optical compensator that can be used is an optical compensator based on the use of liquid crystal materials that can be switched to change the compensation behavior depending on the voltage applied such that the compensation can be optimized depending on the wavelength selected. It is an advantage of particular embodiments of the present invention that the optical compensator used does not rely on diffraction according to different diffraction orders for the different irradiation beams, such that no relation is imposed between the different aberrations to be corrected. The optical compensator may reduce or at least partly compensate aberrations simultaneously for different irradiation beams or may comprise different portions, each portion being adjusted to reduce or at least partly compensate aberrations in an irradiation beam of a specific wavelength or wavelength range. The optical compensator may e.g. be a phase wheel comprising different portions each for compensating or reducing optical aberrations in different irradiation beams of different wavelengths or wavelength ranges. Different optical compensators, such as e.g. a phase wheel or a liquid crystal material based optical compensator may be provided with a control means adapted for selecting a given portion of the optical compensator to be brought into the irradiation beam path in accordance with a selected irradiation beam.

Typically the detection system additionally may comprise a detection unit 110 for detecting and quantifying luminescence responses, obtained by collecting luminescence irradiation beams from the substrate. Such a detection unit may comprise at least one detector, such as a photodetector, a charged coupled device (CCD), a charged injection device (CID), a complementary metal-oxide semi-conductor (CMOS), a photomultiplier tube, an avalanche photodiode, a solid state optical detection device, a microscope or a video camera. The at least one detector may be a number of detectors, adapted for detecting different luminescence irradiation beams collected from the substrate. The at least one detector may be a pixelated detector or a line of multiple single-pixel detectors. Such a detector may e.g. be a charge coupled device (CCD) detector or a CID, a row of photon tube multipliers, a row of avalanche photodiodes or an other irradiation detector that comprises an array of individual detection pixels. The width of the at least one detector or, in case pixelated detectors are used, of the detector elements of the at least one detector typically preferably may be such that detection may occur for spatially distinctive areas on the substrate, whereby the spatially distinctive areas are such that approximately always maximally one occupied binding site is present within the area detected by a single pixel during examination. The latter allows a way of digital detection, i.e. allowing to detect whether or not a given binding site is occupied or not resulting in a binary decision. A typical area detected by a single pixel may be sized between 0.01 $\mu m^2$ and 100 $\mu m^2$, preferably between 0.1 $\mu m^2$ and 25 $\mu m^2$, such as e.g. 1 $\mu m^2$. In a particular embodiment, evaluation unit 111 may be provided for determining a concentration of or distribution of luminescence sites and/or for statistical processing of the obtained detection results, e.g. to correlate two different measurements for checking whether or not lightly bounded luminescence particles have influenced the detection. Such an evaluation means may comprise a processing means, such as e.g. a microprocessor, and/or a memory component for storing the obtained and/or processed evaluation information. Furthermore typical input/output means 112 may be present. The evaluation unit 111 may be controlled using appropriate software or dedicated hardware processing means for executing the evaluation steps. The evaluation means 111 thus may be implemented in any suitable manner, e.g. dedicated hardware or a suitably programmed computer, microcontroller or embedded processor such as a microprocessor, programmable gate array such as a PAL, PLA or FPGA, or similar. The results may e.g. be displayed on any suitable display means 112 such as a visual display unit, plotter, printer, etc. evaluation means 111 may also have a connection to a local area or wide area network for transmission of the results to a remote location.

Other optional components of the detection system 100 may be a focus controlling means 113, e.g. a focusing servo system, and a tracking controlling means 114, e.g. a tracking servo system, for controlling the focusing of the excitation beam and for controlling the position of the excitation beam e.g. on specific tracks. The focus controlling means may be based on different focusing methods, such as for example, but not limited to Foucault wedge focusing. A tracking controlling means 114 typically may be used for controlling tracking, which is needed for obtaining accurate spatial detection. Such systems may comprise actuators. The detection system 100 furthermore may comprise high frequency controlling means and an auxiliary detector such as e.g. a charge coupled device (CCD), which may be used for optimizing the tracking and focusing functions.

The detection system furthermore may comprise, besides the first optical element 25, e.g. the first refractive element 25, which typically is the objective element used for focusing the excitation beam on the sample, other optical elements such as e.g. a beam splitters 103 such as polarization selective or dichroic beam splitters, dichroic filters 104, lenses and/or mirrors 105 for directing light from the source of excitation radiation 112 towards and from the sample, etc. Such additional components especially are introduced if a number of irradiation sources are present adapted for each providing an excitation irradiation beam having a different predetermined wavelength or wavelength range and/or if a number of different luminescence irradiation beams are to be detected using different detectors. A dichroic filter or a dichroic beam splitter may be used for blocking unwanted excitation radiation to be incident on the at least one detector element. The optical elements may be grouped in the irradiation optics 106.

The first aspect of the present invention will now be illustrated by a number of particular embodiments and examples, the invention not being limited thereto.

A first particular embodiment according to the first aspect describes a detection system as described above for the first aspect, wherein the plurality of irradiation beams having different wavelength and arranged as to pass through the same optical element 25, e.g. the same refractive element 25, are excitation irradiation beams. In other words, in the present embodiment, the detection system uses a single optical element, e.g. refractive element for focusing at least two excitation irradiation beams having different wavelength on the substrate. The number of excitation irradiation beams that may be used is not limited, and may e.g. be two, three, four, etc. The excitation irradiation beams may be used simultaneously, i.e. such that excitation fields of the excitation irradiation beams are focused on the substrate 6 at the same time, or one or more excitation irradiation beams may be selected for use from the plurality of excitation irradiation beams. The excitation irradiation beams also may be selected subsequently. The present embodiment comprises an optical compensator 5 for adjusting at least one of the at least two excitation irradiation beams having different wavelength such that optical aberrations induced by the single optical element, e.g. the single refractive element, are reduced or at least partly compensated for. The optical compensator 5 may have the same features and advantages as described above. It may be adapted for reducing or at least partly compensating optical aberrations of the different excitation beams having different wavelength such that the different excitation beams are focused at the same focus on the substrate. It thus may be an advantage according to an embodiment of the present invention that the excitation irradiation beam may be focused appropriately on the substrate, resulting in an efficient and accurate system. The present embodiment will be illustrated by way of a number of examples.

Figure 2:
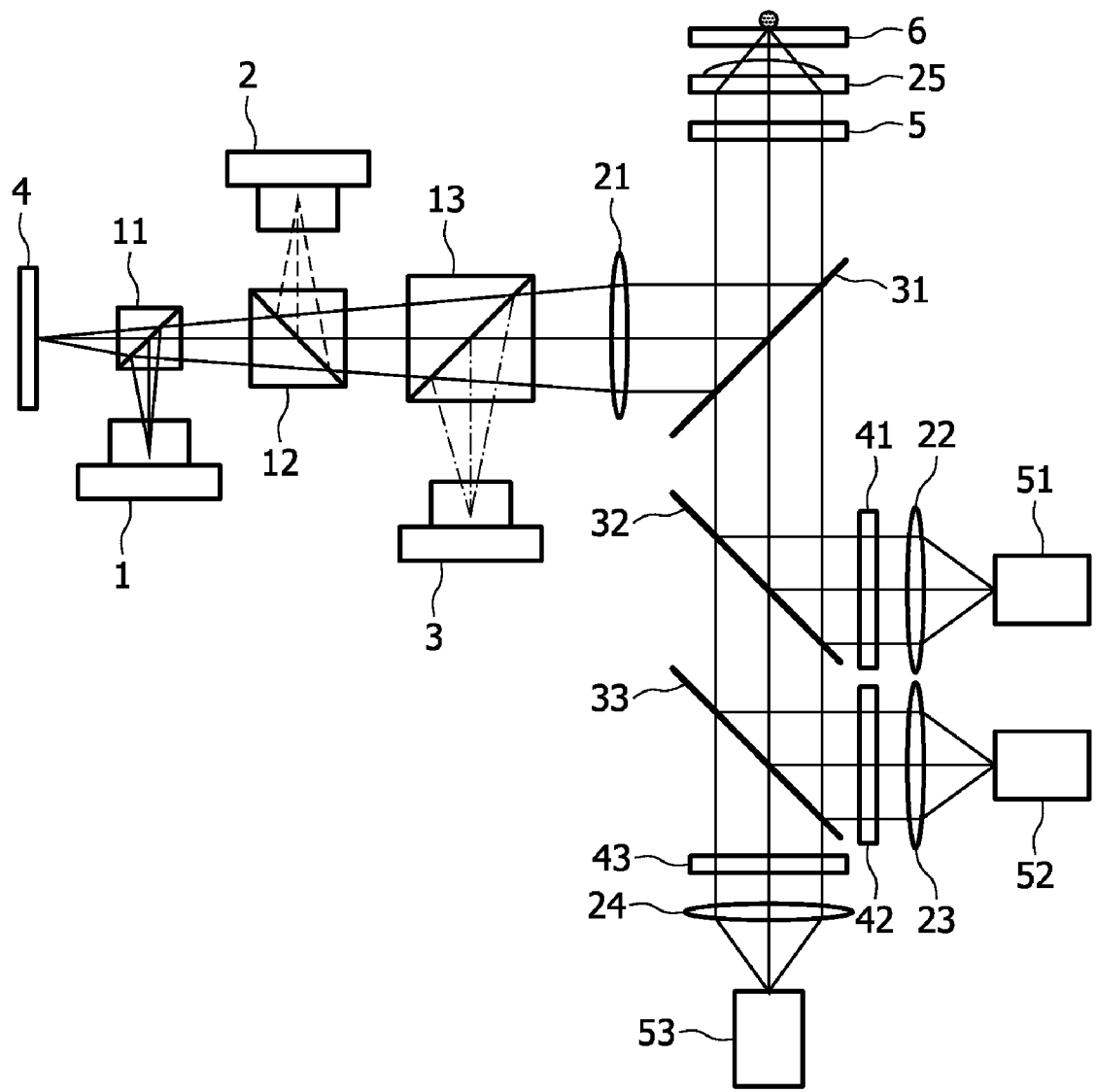
FIG. 2 is a diagrammatic illustration of an optical system of a detection device according to a first embodiment using three excitation irradiation beams to excite up to three labels simultaneously.
Figure 3:
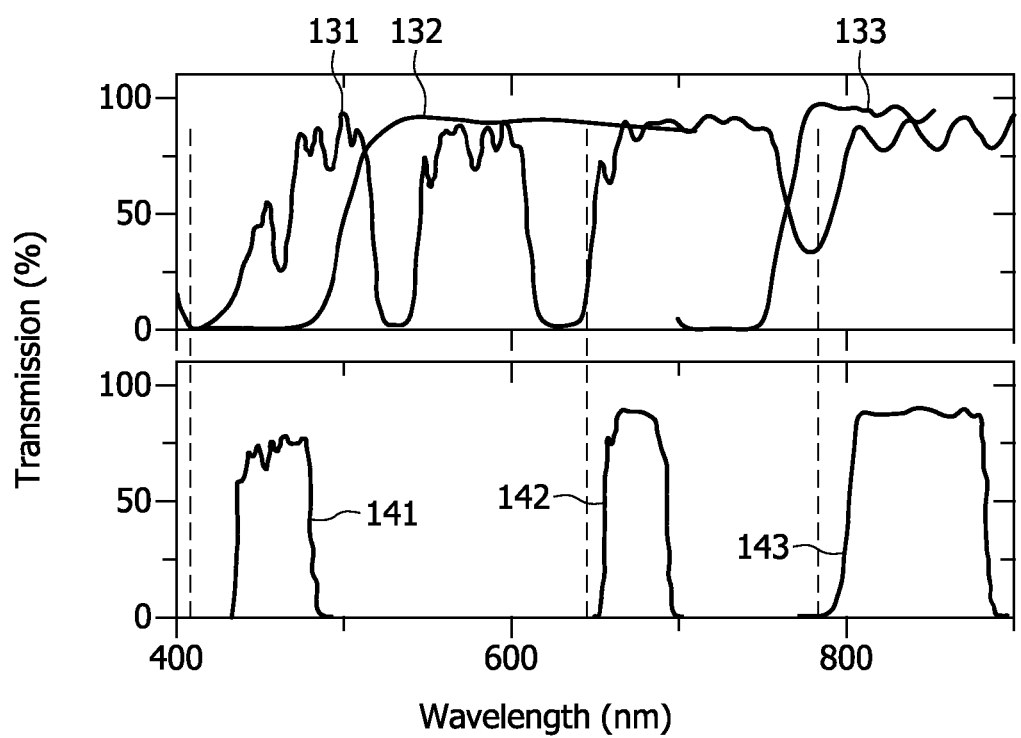
FIG. 3 shows the transmission behavior of an exemplary filter set as can be used in an optical detection system as shown in FIG. 2.

In a first example, a detection system comprises a plurality of excitation irradiation beams enabling excitation with three different excitation irradiation beams each having a different wavelength. In other words, a first irradiation beam has a first, predetermined wavelength $\lambda_1$, a second radiation beam has a second, different, predetermined wavelength $\lambda_2$, and a third radiation beam has a third different predetermined wavelength $\lambda_3$. In the present example, the third wavelength $\lambda_3$ is shorter than the second wavelength $\lambda_2$ and the second wavelength $\lambda_2$ is shorter than the first wavelength $\lambda_1$, although the invention is not limited thereto. In a particular set-up the first, second and third wavelength, $\lambda_1$, $\lambda_2$, $\lambda_3$, respectively, are within the range of approximately 770 to 810 nm for $\lambda_1$, 640 to 680 nm for $\lambda_2$, 400 to 420 nm for $\lambda_3$ and preferably substantially 785 nm, substantially 660 nm and substantially 405 nm, respectively. If the three different wavelengths used are three different wavelengths as often used in optical pick-up units, typically a number of components of such systems may be applied in the detection system, which provides a cost effective way for obtaining such a detection system. Using e.g. a typical optical element, e.g. typical refractive element 25 as used in optical storage systems, the first, second and third radiation beams may have a numerical aperture (NA) of approximately 0.5, 0.65 and 0.85 respectively. As described above, excitation with irradiation beams having a different wavelength may be performed simultaneously, i.e. providing the irradiation beams simultaneously on the substrate, or one or more irradiation beams having a specific excitation wavelength may be selected for use. A system using three excitation irradiation beams is shown by way of example in FIG. 2. By way of example, the invention not being limited thereto, the detection system shown in FIG. 2 furthermore shows a number of detectors for collection of generated luminescence irradiation beams. In the present example, a detection unit for detecting three different luminescence irradiation beams is described, although the detection unit may be adapted for detecting less or more different luminescence irradiation beams. Furthermore, in the present example, the detection system shown is adapted for using a single optical element 25, e.g. single refractive element 25 to both focus the excitation irradiation beams on the substrate and collect the luminescence irradiation beams, although a detection system wherein collection of the luminescence irradiation beams could be done using other optical components is also envisaged by the present embodiment. In the exemplary detection system shown in FIG. 2, the three excitation irradiation beams are generated by three different irradiation sources 1, 2, 3, e.g. three different lasers, operating at three different wavelengths. In the exemplary detection system shown in FIG. 2, the different irradiation paths are partly overlayed using three beam splitters 11, 12, and 13. The excitation irradiation beams are in the present example collimated by a lens 21 although the invention is not limited thereto. A dichroic beam splitter 31 is used to send the irradiation of the different irradiation beams towards an optical compensator 5 and then the first optical element, e.g. first refractive element 25, e.g. objective lens, is used to focus the light onto a substrate 6. The optical compensator 5 is adapted to reduce and/or compensate for optical aberrations occurring by using the same first optical element, e.g. refractive element, for excitation irradiation beams emitting in a different wavelength or wavelength range, resulting in a common focus of the excitation irradiation beams on the substrate 6. The substrate 6 may have a fixed thickness, e.g. a thickness of 0.6 mm although the invention is not limited thereto. The substrate typically comprises luminescence sites. In response to the excitation, luminescence radiation may be generated from luminescence sites on the substrate. In other words, at least one luminescence irradiation beam may be generated in response to the excitation. In the present example, the luminescence radiation excited by excitation irradiation beams having different wavelengths comprises different luminescence irradiation beams of different wavelengths. The luminescence irradiation beams, in the present example, pass through the optical element 25, e.g. refractive element 25 and the first dichroic filter 31 to the detection unit. In the specific example shown in FIG. 2, luminescence radiation with the shortest wavelength, e.g. green emission, may be reflected by a longpass dichroic filter 32 and this light is further filtered by a bandpass filter 41 and focused with a lens 22 on a first detector 51. The fluorescence that passed dichroic filter 32 is then again split by a dichroic mirror 33. Again the shortest wavelengths may be reflected by dichroic filter 33, this passes through a bandpass filter 42 and is focused with a lens 23 on detector 52. The remaining fluorescence also passes a bandpass filter 43 and is focused with lens 24 on the third detector 53. Since there are three different wavelengths used to excite and also three different bands in which the fluorescence has to be detected, the filters that are used preferably have very specific reflection and transmission characteristics. For instance the first dichroic filter 31 has to be reflective for 405, 650, and 780 nm laser lines but has to be transparent for the induced fluorescence. Such multi-band dichroic filters can be obtained e.g. from Omega Filters (www.omegafilters.com). FIG. 3 depicts some spectra 131, 132, 13 for typical standard dichroic filters and some spectra 141, 142, 143 for typical standard bandpass filters that would be suitable for the example of the present embodiment. It is to be noted that these spectra are only provided by way of example, and that tuning of the filter characteristics of the filters may be performed to fit the filters optimally to the specific application. It is to be noted that part of the excitation irradiation focused on the substrate is reflected by the substrate and reflected by the dichroic filter 31. The reflected irradiation may be focused by a lens 21 on a detector 4 of the focusing and tracking means 113, 114 (not shown in FIG. 2) used for focusing and tracking. Since multiple lasers may be used to excite the sample simultaneously, a filter may be placed in front of the focusing and tracking detector 4 to ensure proper tracking by only using a single laser to generate the tracking signal.

Figure 4:
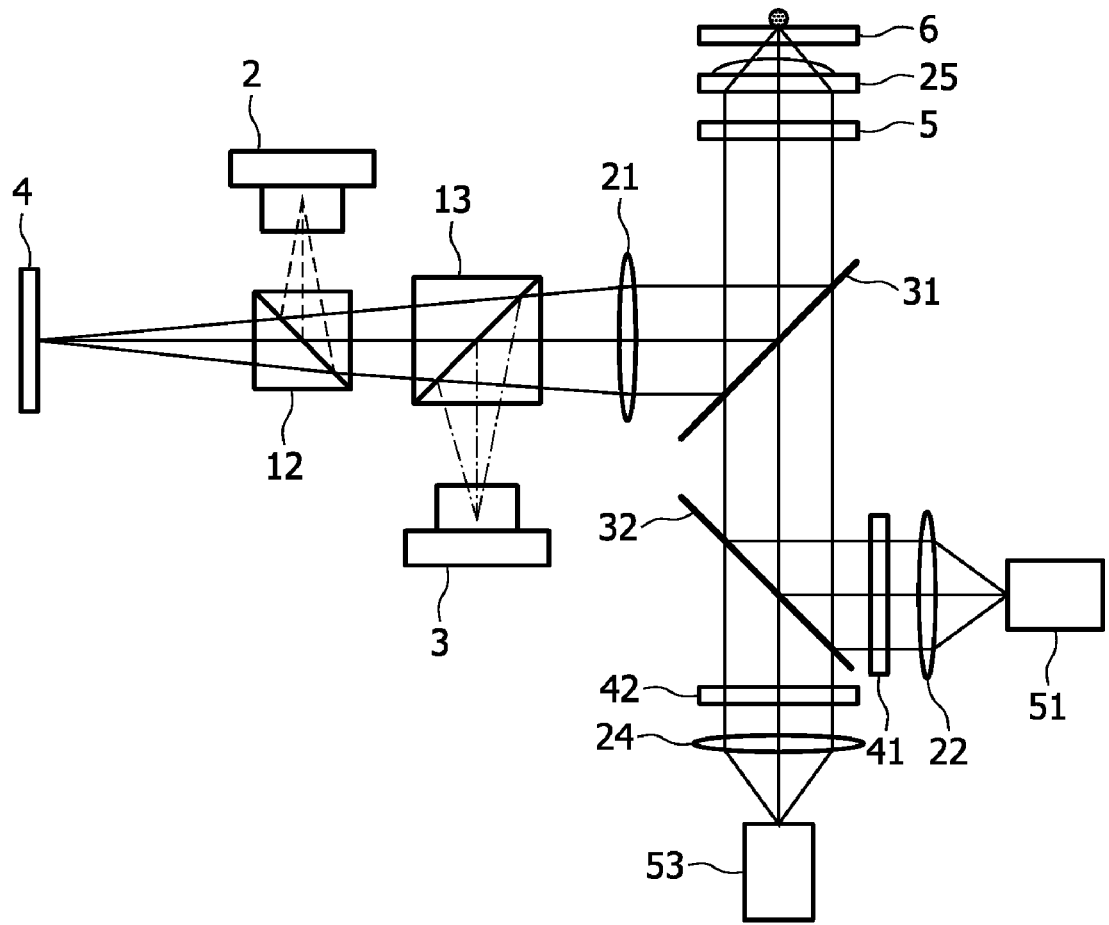
FIG. 4 is a diagrammatic illustration of an alternative optical system of a detection device according to the first embodiment using two excitation irradiation beams to excite up to two labels simultaneously.

According to a second example, the above described detection system operates with only two different irradiation sources 2, 3, e.g. lasers. The exemplary detection system shown in FIG. 4 furthermore comprises two detectors 51, 53 for detecting two distinct luminescence irradiation beams. It is to be noted that in the present example also more or less detectors may be used, depending on the number of luminescence irradiation beams to be detected and depending on the functionality of the detectors used. For most bioassays it is sufficient to use two different labels and thus using only two of the three irradiation sources, e.g. lasers, used in the previous example suffices. Since typically only two fluorescence bands may have to be detected, this simplifies the whole system. In particular, the requirements on the filters 31, 32 used for appropriately guiding the irradiation beams are less stringent. Different combinations of wavelength can be advantageous. Combining irradiation beams with shorter wavelengths will allow detection of smaller detection spots on the sample, as typically the diffraction limit scales with the wavelength. E.g. irradiation beams with wavelengths of e.g. substantially 405 nm and substantially 650 nm results in a higher resolvability of luminescent events than using irradiation beams with wavelengths of e.g. substantially 650 nm and 780 nm. On the other hand, as typically more substances are fluorescent when excited at short wavelengths, using shorter wavelengths might result in a larger background signal. The latter problem thus may be reduced by e.g. using irradiation beams having larger wavelengths, e.g. irradiation beams with wavelengths of e.g. substantially 650 nm and 780 nm.

Figure 5:
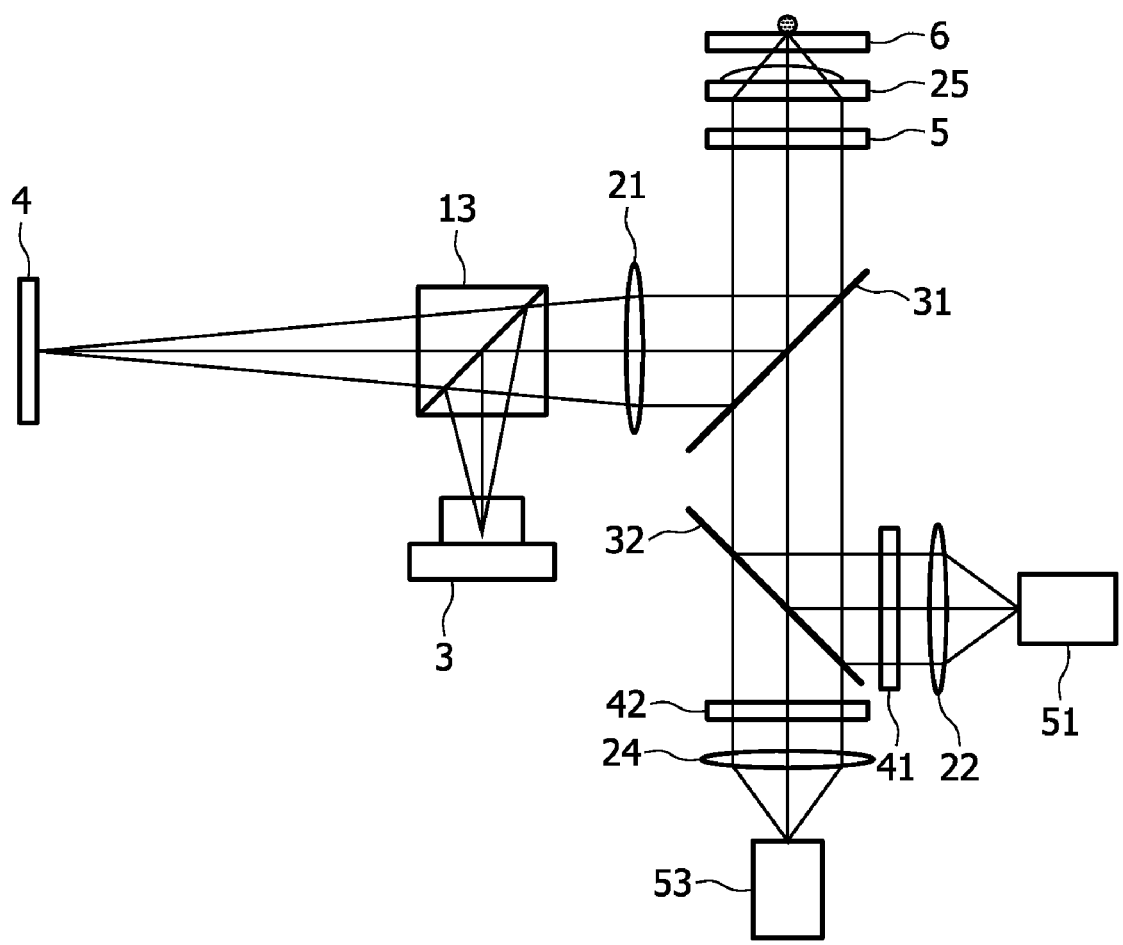
FIG. 5 is a diagrammatic illustration of an optical system of a detection device according to a second embodiment of the first aspect of the present invention using a single excitation irradiation beam and two luminescence irradiation beams enabling FRET measurement.

A second embodiment according to the first aspect of the present invention relates to a detection system as described above, wherein only a single excitation irradiation beam is used, but wherein the optical element 25, e.g. refractive element, used for focusing the single excitation irradiation beam on the substrate is also used for collecting at least one luminescence irradiation beam having a different wavelength than the excitation irradiation beam. The detection system thereby comprises an optical compensator for adjusting at least one of the excitation irradiation beam or the luminescence irradiation beam(s) for optical aberrations induced by the optical element, e.g. refractive element. The second embodiment will be illustrated using an example, the invention not being limited thereto. According to an exemplary detection system according to the second embodiment, as shown in FIG. 5, a single excitation irradiation beam is used to excite the sample 6 and at least one, e.g. two different luminescence irradiation beams are detected from the sample 6. This configuration can be used e.g. in Fluorescence Resonance Energy Transfer (FRET) experiments. In FRET a single laser is used to excite a donor dye. This dye can fluoresce at a first wavelength region, detected by the first detector 51. If, however, an acceptor dye is nearby (less than 5 nm distance) that has an absorption spectrum that overlaps with the emission of the donor dye, the energy can be transferred. The acceptor dye will then fluoresce at a second, red shifted, wavelength region which will be detected by the second detector 53. By monitoring the ratio between the two channels it is possible to measure the distance between the two dyes which can yield important information in for instance real time PCR. An alternative example for using the particular configuration wherein one wavelength excitation occurs combined with multiple wavelength detection can also be useful in other cases, for instance when a combination of fluorescent species are used that can be excited at one common wavelength but will result in spectrally distinct luminescence, examples are for instance Quantum dots. These can be excited in the UV and result in fluorescence at different rather narrow fluorescence intervals.

Figure 6:
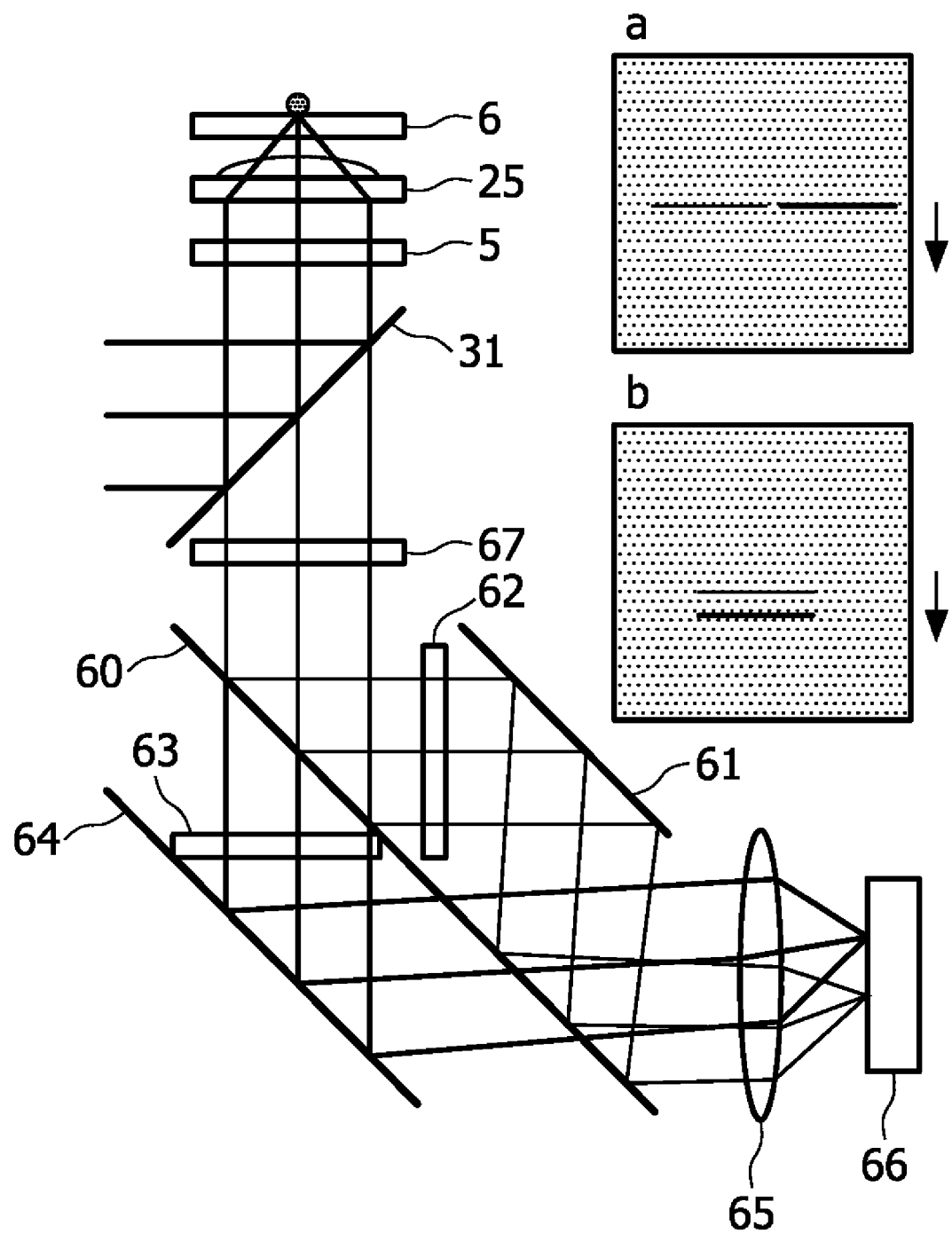
FIG. 6 is a diagrammatic illustration of an optical system of a detection device according to a third embodiment of the first aspect of the present invention enabling two luminescence irradiation beams to be imaged on the same pixelated detector.

In a third embodiment, the present invention relates to a detection system as described above, e.g. a detection system according to the first or second embodiment, but wherein the detection system is adapted for detecting at least two different luminescence irradiation beams having different wavelength using the same pixelated detector. Such a detection system can operate using only a single excitation irradiation beam at a time, e.g. to allow fluorescence resonance energy transfer (FRET), or it can operate using two excitation irradiation beams simultaneously. Typically, the detection system focuses the excitation irradiation beam(s) on the substrate for exciting the sample. The excitation field on the substrate may be of any suitable shape. In a preferred embodiment, it may be of an at least piecewise elongated shape, whereby the excitation field on the substrate may be substantially large compared to diffraction limited spots of a moderate to high numerical aperture objective. The detection system of the present embodiment typically uses an arrangement of filters to allow two color detection such that a parallel read out scheme may be implemented. By way of example, the present embodiment will be illustrated for a detection system generating an at least piecewise elongated shaped excitation field on the substrate, but the invention is not limited thereto and other shapes of the excitation field on the substrate also may be used. In such a detection system, typically a phase plate or a cylindrical lens may be placed in the path of the excitation irradiation beam(s) that adds an additional phase structure on the excitation irradiation beam(s) such that an at least piecewise excitation field, e.g. a thin line or line of excitation dots, is created on the sample, using a standard objective lens as described above. According to the present embodiment, the resulting luminescence responses from the excitation field can be imaged on a detection unit such that the information can be read out in parallel. The luminescence irradiation beams thereby are collected from the sample and guided on at least partly different optical paths such that the different luminescence irradiation beams are imaged on different areas of a pixelated detector. The different luminescence irradiation beams may be focused as parallel luminescence irradiation fields on the pixelated detector, one above the other. The latter has the advantage that the resulting average distance of each of the luminescence irradiation beams to the optical axis of the second, optical element, e.g. refractive element used for focusing the luminescence irradiation beams on the detector is small. The latter is advantageous as the requirements on the second optical element, e.g. refractive element is not that high. Alternatively, the luminescence irradiation beams may be focused on a pixelated detector as neighboring luminescence irradiation fields lying in line. The latter is advantageous for reducing smear which may occur if luminescence detection is performed on two parallel spaced luminescence fields are used, i.e. simultaneous distinct luminescence information may be obtained from the different luminescence irradiation beams. It nevertheless imposes more stringent requirements on the second optical element, e.g. refractive element used for focusing the luminescence irradiation beams on the detector as a wider field of view of the lens is used, and typically more aberrations occur when the distance to the optical axis of an optical element is larger. The present embodiment is illustrated for an exemplary detection system in FIG. 6, showing the illumination collecting part of a detection system. Using a dichroic mirror 31, the luminescence irradiation beams collected from the sample 6 are separated from reflected excitation irradiation. The luminescence irradiation beams pass through the dichroic mirror 31 and may further be purified using an optional filter 67, rejecting e.g. excitation light and increasing the signal/noise ratio. A dichroic mirror 60 then may be used to split the luminescence irradiation beams into two irradiation beams each having a specific wavelength or wavelength range. The first luminescence irradiation beam, in the present example, is reflected and can, after optionally passing through a bandpass filter 62, be guided to a pixelated 2D detector using a tilted mirror 61. The tilted mirror 61 is under a slight angle with respect to the dichroic mirror 60. After reflection by the mirror 61, the light is again reflected by the dichroic mirror 60. The light then enters the second optical element, e.g. refractive element, i.e. focusing lens 65, under a first, small angle with respect to the optical axis, such that the light will be focused slightly off the optical axis on the pixelated sensor 66. The second luminescence irradiation beam passes through the dichroic mirror 60 and can be filtered by an optical bandpass mirror 63. This light is then reflected by a mirror 64 that is placed under a small angle before it passes again through the dichroic mirror 60. It enters the second optical element, e.g. refractive element, i.e. focusing lens 65, under a second, small angle with respect to the optical axis, the second slight angle being different from the first small angle, and is therefore focused at a slightly different position on the camera. For reducing the influence of excitation irradiation, it is either possible to use a single filter at position 67 that lets both luminescence irradiation beams pass but rejects the excitation irradiation beam, or to place two separate filters in the different wavelength bands at positions 62 and 63. The first option has the advantage that only a single filter is needed at an easily accessible position whereas the second option allows a better separation of the two luminescence irradiation beams. It is to be noted that usually the quality of the dichroic mirror is less than that of good bandpass filters resulting in a larger cross-talk if only the dichroic mirror 60 is used to separate the two luminescence irradiation beams. The disadvantage of this arrangement is that the position of the filters might be awkward. It is to be noticed that the set-up discussed above is only exemplary and that a number of different set-ups may lead to a possible parallel read-out scheme according to the present embodiment. This arrangement allows two different irradiation beams of different wavelengths or wavelength regions to be imaged on the same camera. The insets of FIG. 6 show two possible arrangements. In FIG. 6(*a*) a first preferred embodiment is depicted. Luminescence irradiation fields having an at least piecewise elongated shape are imaged horizontally on the camera and the camera is read out from top to bottom. In this arrangement the orientation of mirrors 60, 61, and 64 is such that the lines from the two luminescence irradiation beams are placed next to one another, it is parallel and neighboring or in line. This arrangement has the advantage that during readout the two luminescence irradiation fields will not pass the same area on the detector. Therefore the sample can be illuminated continuously. The disadvantage might be that a larger number of pixels in the horizontal direction is needed. Furthermore, since the information is spread over a larger area, the second optical element, e.g. refractive element such as e.g. focusing lens 65, should have a large field of view to prevent aberrations on the edges.

The second arrangement, shown in FIG. 6(*b*), overcomes these problems by placing the two luminescence irradiation fields in parallel and above one another, it is not in line. Therefore they are both closer to the optical axis of the focusing lens 65 reducing aberrations. The disadvantage is that during readout of the array the information of the first luminescence irradiation beam will pass through the area where the second luminescence irradiation beam is focused. To prevent smear one would have to move the data through this area quickly or block the excitation light momentarily. These solutions might hinder or even prevent continuous readout and movement of the sample.

According to a second aspect, the present invention provides a method for detecting luminescence sites on a substrate, the method including correction for optical aberrations for at least two irradiation beams of different wavelength passing the same optical element, e.g. refractive element, to be focused on or to be collected from the substrate. Such a method for detecting luminescence sites typically comprises generating at least one excitation irradiation beam for exciting luminescence sites on a substrate. The at least one excitation irradiation beam may be a plurality of excitation irradiation beams, such as two, three or more excitation irradiation beams allowing to excite different labels. The plurality of excitation irradiation beams may be generated simultaneously or the excitation irradiation beam having the most appropriate excitation behavior, e.g. the most appropriate excitation wavelength or wavelength range, may be selected for use. The method furthermore comprises guiding, e.g. refracting, at least two irradiation beams of different wavelength with a single optical element, e.g. refractive element, whereby the two irradiation beams may be excitation irradiation beams to be focused on the substrate, luminescence irradiation beams to be collected from excited luminescence sites on the substrate or a combination thereof. Typically by using a single optical element, e.g. refractive element for at least two different irradiation beam of different wavelength, optical aberrations are induced in at least one of the irradiation beams. The method according to the present invention therefore also comprises adjusting one of the at least two irradiation beams of different wavelengths so as to reduce or, if possible, completely compensate for optical aberrations. Typically adjusting one of the at least two irradiation beams of different wavelength may comprise providing an optical path difference in at least one of the at least two irradiation beams of different wavelength. Such an optical path difference may be obtained by inducing a phase shift in at least one of the at least two irradiation beams of different wavelength. The latter may be obtained using an optical compensator. The adjustment of one of the at least two irradiation beams may comprise selecting a specific portion of an optical compensator for correcting for a specific irradiation beam by bringing a specific portion of an optical compensator in the irradiation beam path. Selecting of a specific portion of an optical compensator may e.g. be performed in response to selecting a specific excitation irradiation beam. Alternatively, the adjustment of one of the at least two irradiation beams may comprise simultaneously passing the irradiation beams through an optical compensator whereby all irradiation beams are influenced by the optical compensator, but whereby the effect of the influence is different for at least two irradiation beams. In other words, adjusting may be simultaneously done on the different irradiation beams, e.g. on the different excitation irradiation beams. The method of detection according to the present aspect of the invention may be advantageously performed using a detection system as described in the first aspect of the present invention. In one embodiment according to the second aspect, the present invention relates to a method for detecting luminescence sites on a substrate as described above, wherein at least two excitation irradiation beams are generated and wherein refracting the at least two irradiation beams comprises or consists of focusing the at least two excitation irradiation beams on the substrate. In this embodiment, adjusting at least one of the irradiation beams may be adjusting such that a common focus is reached for both excitation irradiation beams on the substrate.

According to a third aspect, the present invention provides an optical compensator for reducing or at least partly compensating optical aberrations when using different wavelengths in the detection of light emission sites on a substrate. More particularly, an optical compensator is envisaged for adjusting, e.g. selectively adjusting, at least one of at least two incident irradiation beams of different wavelength or wavelength ranges, whereby the optical compensator allows adjusting at least one irradiation beam such that at least two irradiation beams can be focused at a same focus on a surface, e.g. substrate, with a same optical element, e.g. refractive element. Such a surface may be the surface of a substrate to which sample is coupled or e.g. a surface of a detector used for detecting luminescence irradiation beams. In other words, the optical compensator may reduce or at least partly compensate for optical aberrations thus allowing irradiation beams of different wavelengths or wavelength ranges into a common focus. Typically such an optical compensator introduces differences in optical path distance (OPD) for the different irradiation beams in order to correct for the optical aberrations induced by the optical element, e.g. refractive element, used for different irradiation beams of different wavelength. Furthermore, correction for optical aberrations induced by other optical elements also may be performed. The introduction of differences in optical path distance may be e.g. performed by introducing phase shifts. Such phase shifts may be such that for one of the irradiation beams the phase shift, modulo $2\pi$, may be substantially zero, or it may be different from substantially zero for all irradiation beams envisaged. The optical compensator at least partly may compensate, it is it may reduce, the average optical aberrations caused by multiple irradiation beams of different wavelengths. It is an advantage of embodiments of the present invention that the optical compensator can be used in conjunction with optical elements from optical pick-up units for running a number of relevant bioassays in a cost effective manner. The optical compensator may be any suitable optical compensator allowing to at least partly correct for such optical aberrations, such as e.g. a phase plate. The optical compensator may for example be a diffractive element that diffracts the irradiation beams such that the irradiation beam with the shortest wavelength undergoes an introduced phase change (modulo $2\pi$) that is substantially 0, while at least one of the other irradiation beams is diffracted according to a first order diffraction. Another example of an optical compensator may e.g. be a diffractive element having a stepped profile which approximates a blazed diffraction grating, whereby a zero$^{th}$ diffraction order is selected for an irradiation beam with shortest wavelength and a first order and/or higher order diffraction is selected for at least one of the other irradiation beams. The optical compensator 5 for example also may be an optical element comprising non-periodic phase structures (NPSs) for reducing or at least partly compensating a wavefront aberration of at least one of the irradiation beams, whereby the phase structure has birefringent material and has a non-periodic stepped profile. Another example of an optical compensator 5 is based on non-periodic phase structures (NPSs) providing basic radial zone profiles introducing a constant phase across their width superimposed with an additional radial surface profile wherein the non-periodic phase structures introduce a variable phase. In this exemplary optical compensator, the phase changes introduced by the optical compensator may be different from zero for all the irradiation beams, thereby possibly even introducing small aberrations for one irradiation beams, but improving the average amount of aberrations when the optical aberrations for all irradiation beams are taken into account. Still another optical compensator may be based on the use of liquid crystals. It is to be noticed that the above examples of optical compensators are only provided by way of illustration, the present invention not being limited thereto. The optical compensator may be provided in the form of an element separate from an optical element it compensates for, e.g. separate from the objective lens. It should be noted that the optical compensator could also be placed directly on the body of the optical element, e.g. the lens body. It is an advantage of particular embodiments of the present invention that the optical compensator used does not rely on diffraction according to different diffraction orders for the different irradiation beams, such that no relation is imposed between the different aberrations to be corrected.

The optical compensator may reduce or at least partly compensate optical aberrations simultaneously for different irradiation beams or may comprise different portions, each portion being adjusted to reduce or at least partly compensate aberrations for an irradiation beam of a specific wavelength or wavelength range. The optical compensator may e.g. be a phase wheel comprising different portions each for compensating or reducing optical aberrations in different irradiation beams of different wavelengths or wavelength ranges. Some optical compensators, such as a liquid crystal based optical compensator or a phase wheel may be provided with a control means adapted for selecting a given portion of the optical compensator to be brought into the irradiation beam path in accordance with a selected irradiation beam.

Figure 7:
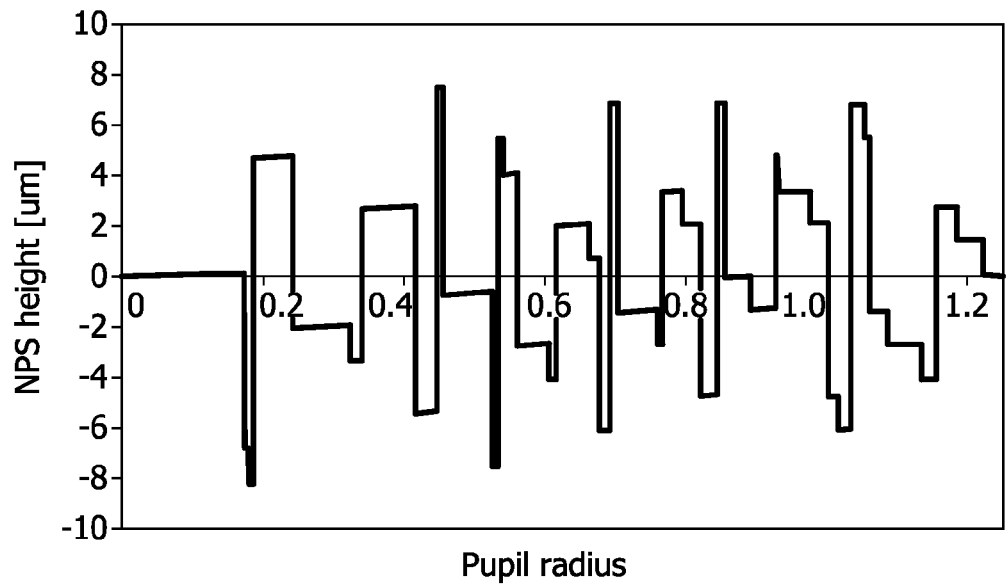
FIG. 7 is a schematic illustration of exemplary non-periodic phase structures along a radius of an optical compensator, according to an embodiment of a third aspect of the present invention.

In a specific example, an optical compensator according to the third aspect of the present invention is shown by way of illustration, the invention not being limited thereto. The optical compensator provided allows for reduction of optical aberrations for three excitation beams of different wavelength or wavelength range. The optical compensator typically includes a planar base substrate on which a non-periodical phase structure (NPS) is formed. The NPS includes a series of annular zones of different heights, each separated by a discrete step of a controlled height. These zones of an NPS introduce a constant phase across the zone and are selected such that, at the position of the step, the zone is substantially invisible to the wavelength of a selected one of e.g. three irradiation beams. In other words, steps can be found which add a phase, modulo 2π, which is equal to zero for one of the wavelengths. The zone widths, and step heights, are chosen to provide a desired compensation of aberrations for the two other wavelengths. Such zone heights $h_j$ (the height of zone j above the base surface of the substrate) are designed to be equal to:

$$h_j = m_j \frac{\lambda}{n-1} \quad (1)$$

where $m_j$ is an integer, $\lambda$ the wavelength and $n_1$ is the refractive index of the material from which the NPS is made, at that wavelength. The above equation is valid where the NPS interfaces with air; the interface could also be between two different materials, in which case the denominator becomes ($n_1$-$n_2$). In a further example, each zone of an NPS structure includes, besides a basic radial zone profile, an additional radial surface profile superimposed on the basic zone profile within each zone, or at least some zones, of the NPS to add variable phase. This additional radial surface profile of a zone provides a height variation within the zone, across its radial width. The additional radial surface profile is non-diffractive. Each height variation within a zone is significantly smaller than the height variations between the zones, which can be taken as the height variation between the average height of the zone and the average height of its adjacent zones. Each height variation within a zone is typically at most a half of the height variation between the average height of the zone and the average height of its adjacent zones. The additional radial surface profile has the effect of further reducing the remaining aberrations, typically spherical aberration, for at least one, more preferably two, of the irradiation beams of different wavelengths, whilst introducing acceptable aberrations for the one wavelength for which the lens design typically is optimized. Alternatively, the lens design may not be optimal for any of the wavelengths. The additional radial surface profile may be the same in each zone or different. As a result, the peak-to-peak remaining optical path differences (OPDs) for each wavelength are preferably less than 0.5 wavelength, more preferably less than 0.4 wavelength and even more preferably less than 0.333 wavelength. Moreover, the maximum remaining OPDs for at least two of the wavelengths are preferably less than 0.333 wavelength, more preferably less than 0.2 wavelength. However, there is remaining high order aberration for each wavelength. Therefore, the peak-to-peak remaining OPD for each wavelength is typically at least 0.05 wavelength, and may be at least 0.1 wavelength or even at least 0.2 wavelength. In another example, the surface within each NPS zone is made aspherical in order to further reduce the remaining aberrations for at least one, more preferably two, of the wavelengths, whilst introducing acceptable aberrations for the one wavelength for which the optical element, e.g. lens, design is optimized. The radial height variations provided by the additional radial surface profiles in this case comprise a gradually varying height variation, beginning at zero at the innermost part of the zone and ending at the largest amount of height variation at the outermost part of the zone. The size of the largest height variation is significantly smaller than the height variations between the zones. Typical step heights that may be used, e.g. in systems wherein irradiation beams of wavelengths $\lambda_1 < \lambda_2 < \lambda_3$ are to be compensated for with a lens optimized for $\lambda_1$ may be within ranges $$h = m * h_1 + \frac{\Delta * \lambda_1}{n_1 - 1}, \quad (2)$$

where $-0.4 < \Delta < 0.4$ with m an integer. By way of example, FIG. 7 shows a radial profile of a possible non-periodic phase structure as can be used for reducing optical aberrations for three different irradiation beams of different wavelengths, in the present example being 408 nm, 660 nm and 790 nm. It is to be noticed that in order to calculate the additional radial surface profile used in each zone, a merit function may be used. The best local zone height is determined for each radial position separately. To achieve this, the local zone height is varied and for each local zone height the merit function is determined. The local zone height with the lowest merit has the highest quality and is chosen as best local zone height for that radius. A high quality for one wavelength ($\lambda_1$, $\lambda_2$, $\lambda_3$) is when the remaining OPD is closest to zero, however the merit function takes into account the quality for each wavelength, and balances the qualities to provide the highest overall quality as measured by the merit function. The remaining OPD is calculated by subtracting the OPD due to the zone height from the OPD that must be corrected and taking a fractional part of this value, so that all remaining OPDs lie between −0.5 wavelength and +0.5 wavelength. An example of a merit function which may be used is the following:

$$\text{Merit} = (W_{\lambda_1} * \text{ROPD}_{\lambda_1}^4) + (W_{\lambda_2} * \text{ROPD}_{\lambda_2}^4) + (W_{\lambda_3} * \text{ROPD}_{\lambda_3}^4) \quad (3)$$

In equation (3), $\text{ROPD}_{\lambda_1}$, $\text{ROPD}_{\lambda_2}$ and $\text{ROPD}_{\lambda_3}$ are the remaining OPDs for the different irradiation beams. They are raised to a given even and positive power, in this example the $4^{th}$ power, in order to ensure that a high remaining OPD at one wavelength is much worse than low remaining OPD at the other wavelength in terms of light loss in the structure. With the weighting factors $W_{xx}$ the contribution for each irradiation beam can be weighted. The merit function selects an optimum solution so that the peak-to-peak remaining OPDs for each wavelength, or at least two of the wavelengths, are preferably less than 0.5 wavelength, more preferably less than 0.4 and even more preferably less than 0.333 wavelength.

According to a fourth aspect, the present invention provides a method for designing an optical compensator such that it can reduce optical aberrations in at least one of at least two incident irradiation beams of different wavelength or wavelength ranges to be focused at a same focus on a substrate when focused with a same optical element, e.g. refractive element. In other words, the present invention provides a method for designing an optical compensator according to the third aspect of the present invention. Designing of the optical compensator thereby is such that features are introduced whereby the optical path difference for at least two incident irradiation beams is such that a common focus may be obtained when the irradiation beams are focused by a single optical element, e.g. refractive element. Such features may e.g. be non-periodic phase structures introduced in a phase plate, whereby heights of these features may be optimized taking into account the optical path different for at least two incident irradiation beams taking into account a common focus of the irradiation beams when focused by a single optical element, e.g. refractive element. Typically such a method comprises obtaining information about the wavelength or average wavelength of the irradiation beams, obtaining information about the position and optical characteristics of an optical element, e.g. refractive element used for focusing the irradiation beams and calculating optimal feature parameters of an optical compensator such that optical aberrations are reduced for the irradiation beams taking into account that a same focus is to be obtained for the irradiation beams focused by the single optical element, e.g. refractive element. Calculating optimal feature parameters may be done by simulation, using predetermined algorithms, using neural networks or in any other suitable way. It may be done in an automatic and/or automated way.

Figure 8:
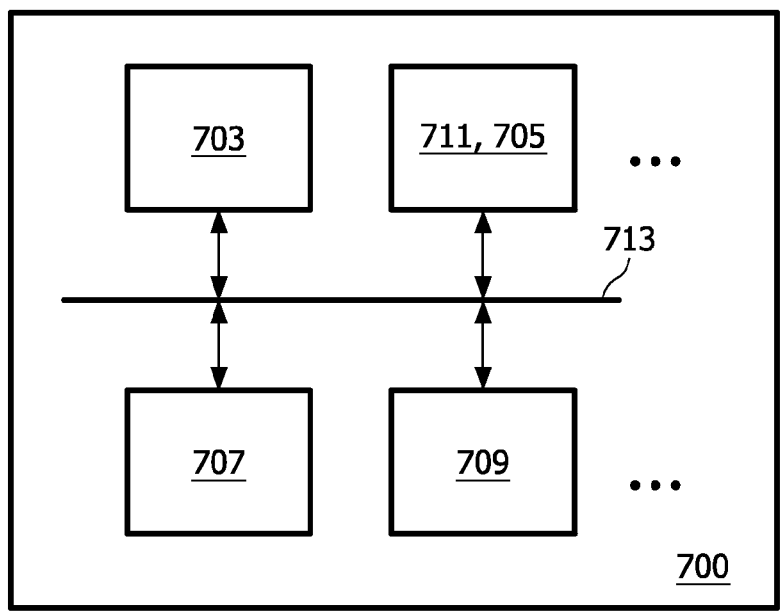
FIG. 8 is a schematic illustration of a processing system that may be used for performing a method of designing an optical compensator according to a further embodiment of a fourth aspect of the present invention.

The above-described design method according to the fourth aspect of the present invention may be implemented in a processing system 700 such as shown in FIG. 8. FIG. 8 shows one configuration of processing system 700 that includes at least one programmable processor 703 coupled to a memory subsystem 705 that includes at least one form of memory, e.g., RAM, ROM, and so forth. A storage subsystem 707 may be included that has at least one disk drive and/or CD-ROM drive and/or DVD drive. In some implementations, a display system, a keyboard, and a pointing device may be included as part of a user interface subsystem 709 to provide for a user to manually input information. Ports for inputting and outputting data also may be included. More elements such as network connections, interfaces to various devices, and so forth, may be included, but are not illustrated in FIG. 8. The various elements of the processing system 700 may be coupled in various ways, including via a bus subsystem 713 shown in FIG. 8 for simplicity as a single bus, but will be understood to those in the art to include a system of at least one bus. The memory of the memory subsystem 705 may at some time hold part or all (in either case shown as 711) of a set of instructions that when executed on the processing system 700 implement the steps of the design method described herein. Thus, while a processing system 700 such as shown in FIG. 8 is prior art, a system that includes the instructions to implement aspects of the methods for designing an optical compensator is not prior art, and therefore FIG. 8 is not labeled as prior art.

It is to be noted that the processor 703 or processors may be a general purpose, or a special purpose processor, and may be for inclusion in a device, e.g., a chip that has other components that perform other functions. Thus, one or more aspects of the present invention can be implemented in digital electronic circuitry, or in computer hardware, firmware, software, or in combinations of them. Furthermore, aspects of the invention can be implemented in a computer program product tangibly embodied in a carrier medium carrying machine-readable code for execution by a programmable processor. The term "carrier medium" refers to any medium that participates in providing instructions to a processor for execution. Such a medium may take many forms, including but not limited to, non-volatile media, and transmission media. Non volatile media includes, for example, optical or magnetic disks, such as a storage device which is part of mass storage. Volatile media includes mass storage. Volatile media includes dynamic memory such as RAM. Common forms of computer readable media include, for example a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read. Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infrared signal. An infrared detector coupled to a bus can receive the data carried in the infrared signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN or the Internet. Transmission media can take the form of acoustic or light waves, such as those generated during radio wave and infrared data communications. Transmission media include coaxial cables, copper wire and fiber optics, including the wires that comprise a bus within a computer.

Applications of the present invention can be in the field of molecular diagnostics: clinical diagnostics, point-of-care diagnostics, advanced biomolecular diagnostic research, biosensors, gene and protein expression arrays, environmental sensors, food quality sensors, etc. The present invention allows a large number of useful bioassays to be run in a cost-effective package.

Multiple chromogenic labels also may be used in microarray technology, flow cytometry, detection based on fluorescence resonance energy transfer (FRET) which occurs due to the interaction between the electronic excited states of two chromogenic dye molecules, molecular beacons based detection technology such as e.g. real-time nucleic acid detection and real-time PCR quantification, surface enhanced detection techniques such as surface-enhanced Raman spectroscopy (SERS), surface-enhanced fluorescence (SEF) or surface-enhanced resonance Raman spectroscopy (SERRS), microfluidic detection, etc.

In preferred embodiments, the detection system of the present invention is an epi-fluorescence biosensor meaning that the light is incident on the surface from above, but it could also be a transmission biosensor, meaning that the light is incident from below and transmitted through the microarray.

As indicated above, embodiments of the present invention provide or use an optical compensator for detection methods which involve multiple wavelengths to be focused into a common focal point. In today's high through-put molecular diagnostics there is a need to detect multiple labels simultaneously, and the present invention provides a cost effective solution thereto. The wavelength shifts generated by these excitable labels result in multiple wavelengths that are generally different to the irradiation beam for which aberration correction is crucial if sensitive detection of individual labels is the goal.

An advantage of particular embodiments of the present invention is that different labels can be used and detected simultaneously because optical aberrations that normally occur with multiple wavelength detection systems are now reduced or at least partly compensated for by provision of an appropriately designed optical compensator.

Other arrangements for accomplishing the objectives of multiple wavelength focusing embodying the invention will be obvious for those skilled in the art. It is to be understood that although preferred embodiments, specific constructions and configurations, as well as materials, have been discussed herein for devices according to the present invention, various changes or modifications in form and detail may be made without departing from the scope and spirit of this invention.

The invention claimed is:

1. A detection system for detecting luminescence sites on a substrate, the detection system comprising:
    an irradiation unit for generating at least one excitation irradiation beam for exciting luminescence sites on the substrate;
    a refractive optical element for
        receiving at least two irradiation beams of different wavelengths or wavelength ranges, the at least two irradiation beams are excitation irradiation beams,
        focusing the at least two irradiation beams on a substrate, and
        collecting luminescence irradiation beams from the excited luminescence sites on the substrate; and
    an optical compensator for adjusting at least one of the at least two irradiation beams of different wavelengths or wavelength range so as to at least partly compensate for optical aberrations.

2. The detection system according to claim 1, wherein said irradiation unit is adapted for generating at least two excitation irradiation beams of different wavelength or wavelength range.

3. The detection system according to claim 1, said optical compensator introducing at least a phase shift in one of said irradiation beams.

4. The detection system according to claim 2, wherein said optical compensator introduces at least a phase shift in one of said excitation irradiation beams for focusing said excitation irradiation beams at the same focus point on the substrate.

5. The detection system according to claim 1, wherein said optical compensator and said refractive optical element are separate elements.

6. The detection system according to claim 1, wherein said optical compensator is incorporated into the refractive optical element.

7. The detection system according to claim 2, wherein one of said at least two irradiation beam is selected to be used at a time.

8. The detection system according to claim 1, wherein said irradiation unit is adapted for generating at least two of said at least two excitation irradiation beams simultaneously.

9. The detection system according to claim 8, further comprising a detection unit having at least a detector element and optical elements for focusing said at least two luminescence irradiation beams as parallel luminescence irradiation fields on the detector element.

10. The detection system according to claim 8, further comprising a detection unit having at least a detector element and optical elements for focusing said at least two luminescence irradiation beams as neighboring luminescence irradiation fields lying in line on the substrate.

11. The detection system according to claim 1, further comprising a detection unit adapted for simultaneously detecting different luminescence irradiation beams from said luminescence sites, said different luminescence irradiation beams each having a substantially different wavelength.

12. The detection system according to claim 2, said at least two excitation irradiation beams including a first, a second and a third irradiation beams having an average wavelength in a wavelength ranges of 760 nm to 800 nm, 640 nm to 680 nm, and 380 nm to 420 nm, respectively.

13. An optical compensator comprising:
    a refractive optical element for
        adjusting at least one of at least two incident irradiation beams of different wavelength or wavelength range;
        focusing said at least two incident irradiation beams at a same focus point on a substrate.

14. The optical compensator according to claim 13, included in non-periodic phase structures.

15. The optical compensator according to claim 13, comprising a phase wheel having different non-periodic phase structures through which the at least two irradiation beams are arranged to pass.

16. A method for detecting radiation sites on a substrate, the method comprising acts of:
    generating at least one excitation irradiation beam for exciting luminescence sites on the substrate;

guiding at least two irradiation beams of different wavelength or wavelength range, said at least two irradiation beams are excitation irradiation beams to a refractive optical element;
the refractive optical element
   focusing the at least two irradiation beams on the substrate and
   collecting luminescence irradiation beams from the excited luminescence sites on the substrate;
adjusting one of the at least two irradiation beams of different wavelengths or wavelength ranges so as to at least partly compensate for optical aberrations.

17. The method according to claim 16, wherein
at least two excitation irradiation beams are generated, and
at least one of said at least two excitation irradiation beams is adjusted to create a common focus on the substrate.

* * * * *